United States Patent
Toribio et al.

(10) Patent No.: US 7,520,160 B1
(45) Date of Patent: Apr. 21, 2009

(54) ELECTROCHEMICAL SENSOR

(75) Inventors: Michael M Toribio, Al Khobar (SA); Akira Kamiya, Kanagawa-Ken (JP); Stephane Vannuffelen, Hampshire (GB); Noriyuki Matsumoto, Kanagawa-Ken (JP); Jimmy Lawrence, Cambridge, MA (US)

(73) Assignee: Schlumberger Technology Corporation, Sugar Land, TX (US)

( * ) Notice: Subject to any disclaimer, the term of this patent is extended or adjusted under 35 U.S.C. 154(b) by 0 days.

(21) Appl. No.: 11/867,673

(22) Filed: Oct. 4, 2007

(51) Int. Cl.
*G01N 7/00* (2006.01)
(52) U.S. Cl. .................................... 73/31.05
(58) Field of Classification Search ............ None
See application file for complete search history.

(56) References Cited

U.S. PATENT DOCUMENTS

| | | | |
|---|---|---|---|
| 3,780,575 | A | 12/1973 | Urbanosky |
| 3,859,851 | A | 1/1975 | Urbanosky |
| 4,994,671 | A | 2/1991 | Safinya |
| 5,391,839 | A * | 2/1995 | Lang et al. .................. 174/540 |
| 6,582,251 | B1 | 6/2003 | Burke |
| 2005/0029125 | A1 | 2/2005 | Jiang et al. |
| 2005/0186823 | A1 | 8/2005 | Ring et al. |
| 2005/0202720 | A1 | 9/2005 | Burke et al. |
| 2006/0113188 | A1 * | 6/2006 | Mori et al. .................. 204/431 |

FOREIGN PATENT DOCUMENTS

| | | |
|---|---|---|
| GB | 2371651 A | 7/2002 |
| GB | 2397651 A | 7/2004 |
| GB | 2404252 A | 1/2005 |
| GB | 2409902 A | 7/2005 |
| WO | 2004011929 | 2/2004 |
| WO | 2004063743 | 7/2004 |
| WO | 2005020272 | 3/2005 |
| WO | 2005083846 | 9/2005 |

OTHER PUBLICATIONS

Rob Badry, Elton Head, Charles Morris, Ian Traboulay, "New Wireline Formation Tester Techniques and Applications", Trans. SPWLA 34th Annual Logging Symposium, Calgary, Jun. 1993, Paper ZZ, pp. 1-15.

(Continued)

*Primary Examiner*—Robert R Raevis
(74) *Attorney, Agent, or Firm*—Matthias Abrell; Jaime Castano; Dale Gaudier

(57) ABSTRACT

An electrochemical sensor for measuring contents of a fluid or gas at high pressure and/or high temperature, for use, for example, in a wellbore for hydrocarbon applications, is provided. The sensor includes: a bulkhead-like electrode assembly including a cylindrical housing and a cylindrical electrode structure. The cylindrical electrode structure includes a cylindrical conductive pin extending from a high pressure region to a low pressure region and an electrode connected to one end of the pin at the high pressure region and having an electrode surface for exposure to a flow path of the fluid or gas in the high pressure region. At least a part of the surface of the pin is protected from direct contact with the fluid or the gas by an insulating coating impermeable to the fluid or gas. The pin may include an alternating pattern of protruding and receded portions.

7 Claims, 11 Drawing Sheets

OTHER PUBLICATIONS

Brondel D, Edwards R, Hayman A, Hill D, Mehta S, Semerad T. "Corrosion in the oil industry" Oilfield Review pp. 4-18.

Fujishima A, Einaga Y, Rao TN, Tryk D., "Diamond Electrochemistry", Elsevier, Tokyo 2005.

Giovanelli D, Lawrence N, Compton R. "Electrochemistry at High Pressure: A Review", Electroanalysis Oct. 16, 2004, pp. 789-810.

Lawrence N, Davis J, Marken F, Jiang L, Jones TGJ, Davies S, Compton R. "Electrochemical detection of sulphide: a novel dual flow cell", Sensors and Actuators B 69 (2000), pp. 189-192.

Wang, J., "Analytical Electrochemistry," 2nd Ed., Wiley-VCH, New York, 2000.

* cited by examiner

110

120

ELECTROCHEMICAL SENSOR

BACKGROUND OF THE INVENTION

The present invention relates to an electrochemical sensor operable at high temperature and/or high pressure conditions.

Quantitative measurements and evaluation of wellbore fluids are important aspects of determining the quality and economic value of the well. More recently, studies aiming to characterize contents of corrosion-causing components such as H2S, CO2, pH and scale-forming ion species have been reported. This has been driven largely by the need to come up with effective mitigation of the severe impact of corrosion to both oil field operations and investments.

Among the various techniques identified to measure the corrosion contents of wellbore fluids is electrochemical sensing. However, to date, research on high pressure and high temperature electrochemistry has been limited by factors such as corrosion, thermoelectric effects and the decomposition of most polymeric materials. As a result, there still is a great need for thermodynamic data about hydrothermal solutions at high pressure and high temperature conditions such as that of a wellbore. Commercially available press fitted electrodes are limited to use mostly at ambient temperature and pressure conditions due to the eventual penetration of the electrolyte or sensing solution in addition to the wellbore fluids into the small gap found between the electrode materials and the main body.

Earlier designs of sensors specifically for downhole well applications have been reported in Great Britain patent application publication numbers GB2,397,651A, GB2,404,252A and GB2,409,902A and international patent publication numbers WO2004011929 and WO 2004063743.

However, it has recently been confirmed through experimental evaluations that the previously suggested electrode manufacturing methods have problems in applications in extreme wellbore conditions.

Designs that involve press-fitting and/or simple metal mounting procedures on top of electrical pin connectors have failed to obtain the much needed sensor stability and robustness, especially for high temperature and high pressure conditions. Persistent creeping problems, where the liquid electrolyte penetrates into polymer sealant down to the electrical pin sections, have been consistently encountered. This mechanical design failure results in increased background response, or unwanted peak signals related to metal stripping, thus rendering the sensing technique useless, especially at high pressure conditions.

SUMMARY OF THE INVENTION

The invention has been made in view of the foregoing situation, with an object to provide a novel electrochemical sensor design for application in high pressure and high temperature electrochemical sensing.

Briefly stated, the invention achieves its objective by providing a novel design of an electrochemical sensor that would be subsequently used for sensing or measuring contents of a specified component in a fluid or a gas in a high pressure condition and/or high temperature condition. The specified component may include but is not limited to hydrogen sulfide, carbon dioxide, and low or high pH and scale forming ion species in hydrocarbon in wellbore conditions.

An electrochemical sensor for measuring contents of a specified component in a fluid or a gas according to an embodiment of the present invention includes a bulkhead-like electrode assembly having preferably a cylindrical housing and preferably a cylindrical electrode structure in the cylindrical housing, and a seal ring extending around the cylindrical housing of the electrode assembly to serve as a barrier between a high pressure region and a low pressure region when the bulkhead-like electrode assembly is deployed in high pressure and/or high temperature conditions.

According to one aspect of the present invention, the cylindrical electrode structure includes a cylindrical conductive pin extending from the side of the electrode assembly residing at the high pressure region to the side of the electrode assembly at the low pressure region. An electrode is electrically, and preferably also mechanically connected to one end of the cylindrical conductive pin, and resides at the side of the electrode assembly that is designated for exposure to the high pressure region.

According to an aspect of the present invention a least a part of the exterior surface of the conductive pin closer to the electrode is coated with an insulating coating which functions as a barrier to fluid or gas to protect the conductive pin from direct contact with the fluid or the gas. In one preferred embodiment, the electrode is also coated with the insulating coating.

Thus, the conductive pin can be protected from direct contact with fluid or gas even if the fluid or the gas penetrates into the cylindrical housing when the electrode faces high pressure and high temperature conditions.

Other features and advantages of the present invention will become apparent from the following description of the invention which refers to the accompanying drawings.

BRIEF DESCRIPTION OF THE DRAWINGS

The above and other objects, advantages and features of the present invention will be more apparent from the following description taken in conjunction with the accompanying drawings, in which.

DETAILED DESCRIPTION OF EMBODIMENTS OF THE INVENTION

Figure 1:
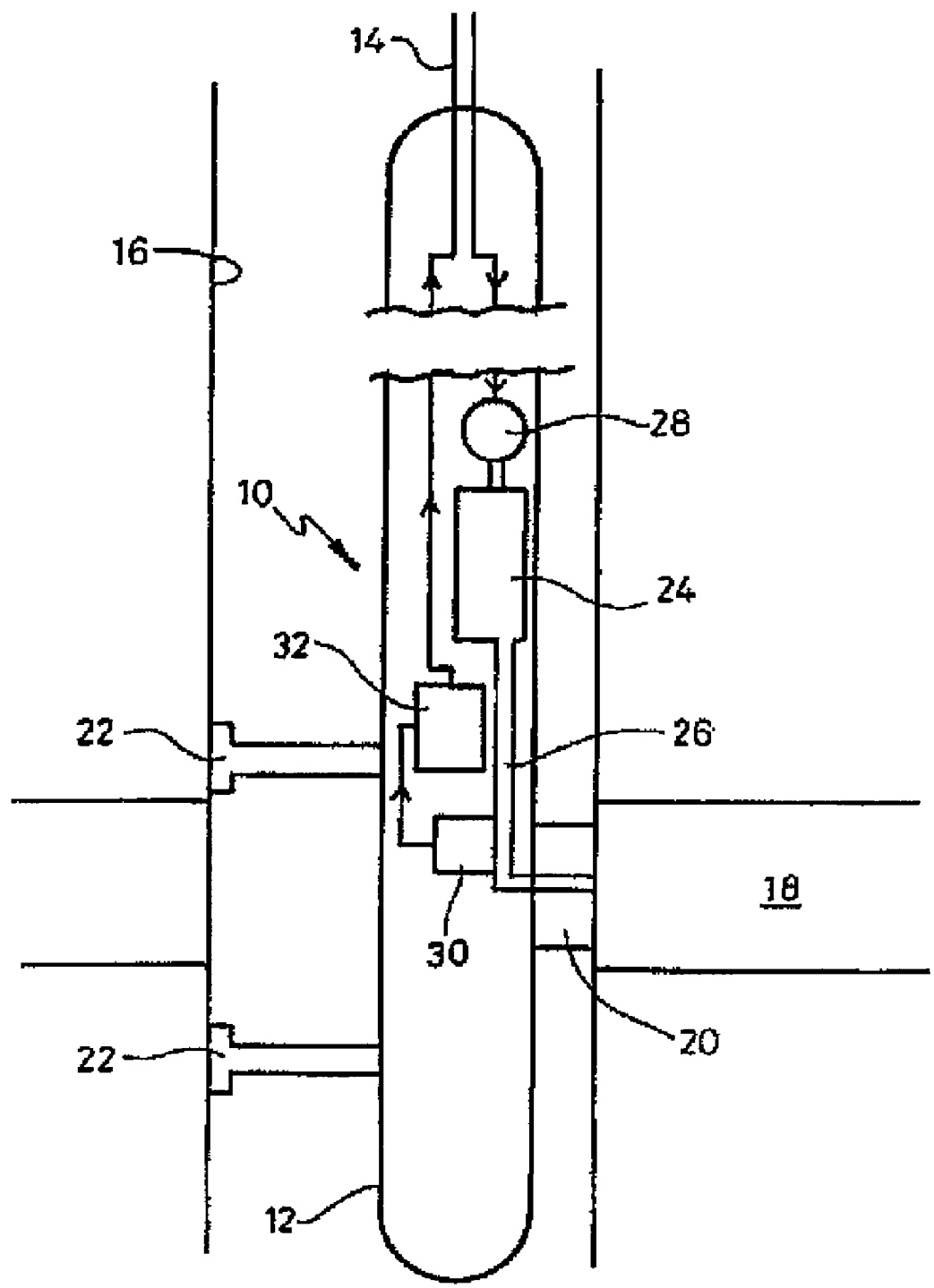
FIG. 1 shows a structure of a wellbore tool.

The invention will be now described with reference to illustrative embodiments. Those skilled in the art will recognize that many alternative embodiments can be accomplished using the teachings of the present invention and that the invention is not limited to the embodiments illustrated for explanatory purposes.

It is to be noted that, in the explanation of the drawings, the same components will be given with the same reference numerals, omitting the repeated explanation.

FIG. 1 shows the structure of a wellbore tool 10. The wellbore tool 10 is based on Schlumberger's Modular Dynamics Tester (MDT) (Schlumberger trademark), as described in U.K. patent publication number 2397651A. The wellbore tool 10 of the present embodiment is used for sensing or measuring contents of a specified component in hydrocarbons in a high pressure condition and/or a high temperature condition.

The tool 10 includes an elongate substantially cylindrical body 12, which in operation is suspended on a wireline 14 in the wellbore 16, adjacent an earth formation 18 believed to contain recoverable hydrocarbons for example, and which is provided with a radially projecting sampling probe 20. To operate tool 10, the sampling probe 20 is placed into firm contact with the earth formation 18 by hydraulically operated rams 22 projecting radially from the body 12 on the opposite side from the sampling probe 20, and is connected internally of the body 12 to a sample chamber 24 by a conduit 26.

In use, and prior to completion of the well constituted by the wellbore 16, a pump 28 within the body 12 of the tool 10 can be used to draw a sample of the hydrocarbons into the sample chamber 24 via the conduit 26. The pump 28 is controlled from the surface at the top of the wellbore 16 via the wireline 14 and control circuitry (not shown) within the body 12. It will be appreciated that this control circuitry also controls valves (not shown) for selectively routing the sampled hydrocarbons either to the sample chamber 24 or to a dump outlet (not shown), but these have been omitted for the sake of simplicity.

In accordance with one embodiment of the present invention, the conduit 26 additionally communicates with an electrochemical sensor 30 also provided within the body 12 of the tool 10, so that the hydrocarbons flow over a face of the electrochemical sensor 30 on their way through the conduit 26.

The sampling probe 20 is located close to the electrochemical sensor 30. The electrochemical sensor 30 produces an output current, which is dependent on the amount of components including but not limited to hydrogen sulfide, carbon dioxide, and pH and scale forming ion species in the hydrocarbons in a high pressure condition flowing through the conduit 26. This output current is measured in a known manner by a digital current measuring circuit 32 in the body 12 of the tool 10, and the measurement is transmitted to the surface via the wireline 14.

Figure 2:
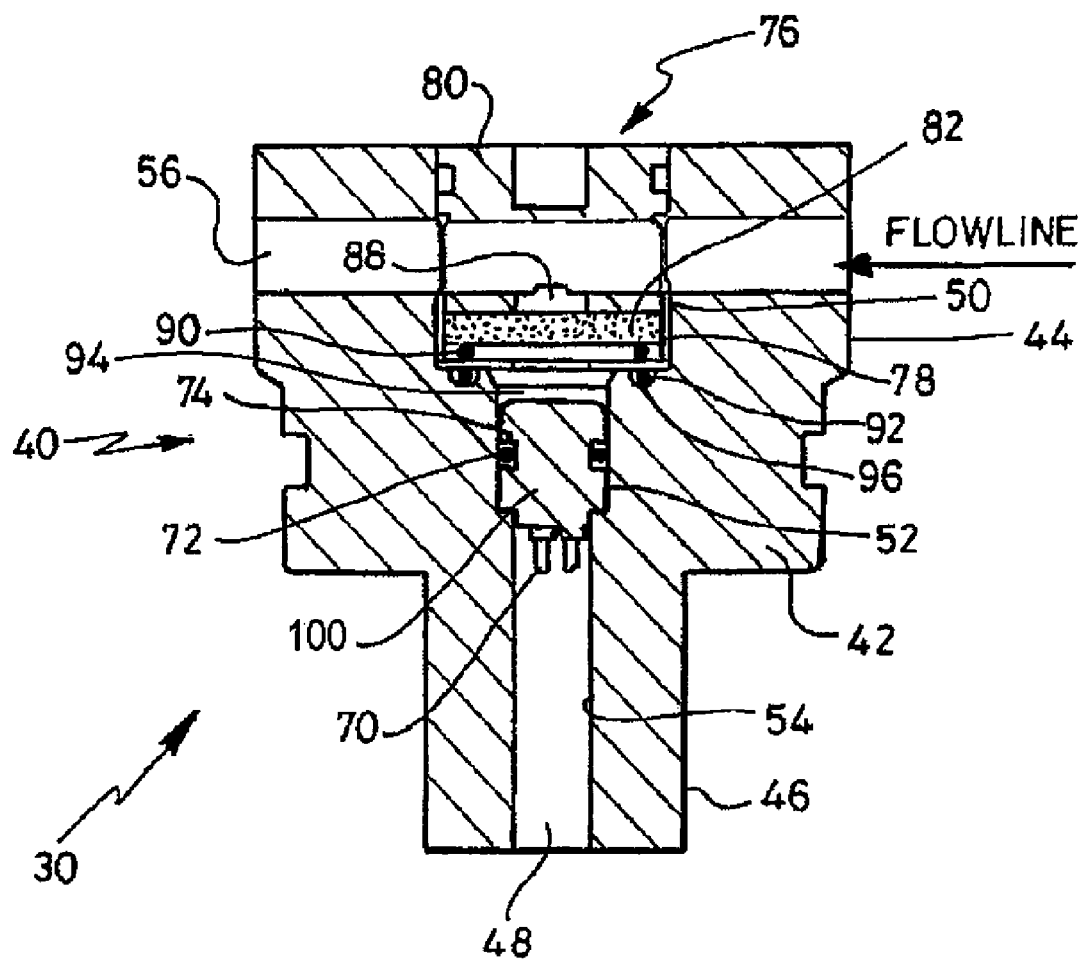
FIG. 2 shows an electrochemical sensor in more detail.

The electrochemical sensor 30 is shown in more detail in FIG. 2. In one embodiment, the electrochemical sensor 30 includes a generally cylindrical housing 40, which may be made from polyetheretherketone (PEEK) and which includes a main housing member 42 having an upper portion 44 (as viewed in the drawings), a reduced diameter lower portion 46, and a stepped diameter cylindrical bore 48 extending coaxially through it from top to bottom. The bore 48 has a large diameter upper portion 50 wholly within the upper portion 44 of the main housing member 42, an intermediate diameter portion 52 also wholly within the upper portion of the main housing member, and a reduced diameter portion 54 largely within the lower portion 46 of the main housing member 42.

A flowpath 56 for the fluid whose content of the components including but not limited to hydrogen sulfide, carbon dioxide, and pH and scale forming ion species is to be sensed extends diametrically through the upper portion 44 of the main housing member 42, intersecting the upper portion of the bore 48.

Disposed in the intermediate diameter portion 52 of the bore 48, and resting on the shoulder defined between the reduced diameter portion 54 and the intermediate diameter portion 52, is a cylindrical electrode assembly 100. The electrode assembly 100 includes a cylindrical mold resin housing for example made of PEEK and a plurality of electrodes including a working electrode, a reference electrode and a counter/guard electrode, which are electrically connected to electrical leads 70, which exit the main housing 30 via the reduced diameter portion 54 of the bore 48. The detailed structure of the electrode assembly 100 will be explained later.

A seal ring, an O ring 72 in this embodiment, made of VITON™ is disposed in a groove 74 extending coaxially round the body of the electrode assembly 100 to seal the electrode assembly 100 within the intermediate diameter portion 52 of the bore 48.

Disposed in the large diameter upper portion 50 of the bore 48, and resting on the shoulder defined between the intermediate diameter portion 52 and the large diameter upper portion 50 is a cylindrical membrane retainer assembly 76. The cylindrical membrane retainer assembly 76 includes a cup-shaped housing member 78, a cylindrical housing member 80 which screws part of the way into the cup-shaped housing member 78, and a gas permeable membrane 82 in the form of a circular plate made of zeolite or other suitable ceramic material coaxially located in the cup-shaped housing member 78, in the space between the bottom of the inside of the cup shape of the housing member 78 and the bottom of the housing member 80.

The housing member 80 has a diametrically extending flow path (not shown) therethrough, and the housing member 78 has diametrically opposed ports (not shown) aligned with the opposite ends of the flow path of the housing member 80, the flow path of the housing member 80 and the ports of the housing member 78 being aligned with the flow path 56 in the upper part 44 of the main housing member 42. The housing member 80 further includes a short duct 88 communicating between the flow path thereof and the bottom of the housing member 80, and therefore communicating with the upper surface of the membrane 82.

The bottom of the housing member 80 is flat, and bears on the upper surface of the membrane 82, pressing it toward the bottom of the inside of the housing member 78. An O-ring seal 90 made of VITON™, for example, is trapped between the lower surface of the membrane 82 and the bottom of the inside of the housing member 78 to provide sealing around the entire periphery of the lower surface of the membrane 82, while the flat bottom of the housing member 80 and the upper surface of the membrane 82 provides a seal around the entire periphery of the upper side of the membrane 82. A further O-ring seal 92 also made of VITON™, for example, is disposed in a groove 96 formed coaxially in the shoulder defined between the intermediate diameter portion 52 and the large diameter portion of the bore 48, and is trapped between the underside of the bottom of the housing member 78 and the shoulder.

The generally cylindrical space beneath the underside of the membrane 82 and the top of the electrode assembly 100 constitutes a reaction chamber, and is filled with a reaction solution containing a precursor or catalyst, for example, dimethylphenylenediamine (DMPD).

The sealing of the membrane 82 in the housing members 78 and 80 using a surface-to-surface seal and the O-ring seal 90, coupled with the sealing provided by the O-ring seal 92, ensures that the reaction solution is not washed out of the chamber 94 by the hot, high pressure hydrocarbons in the flow path 56, while the materials used, in particular for the membrane 82, are also able to withstand the hostile borehole environment.

Figure 3:
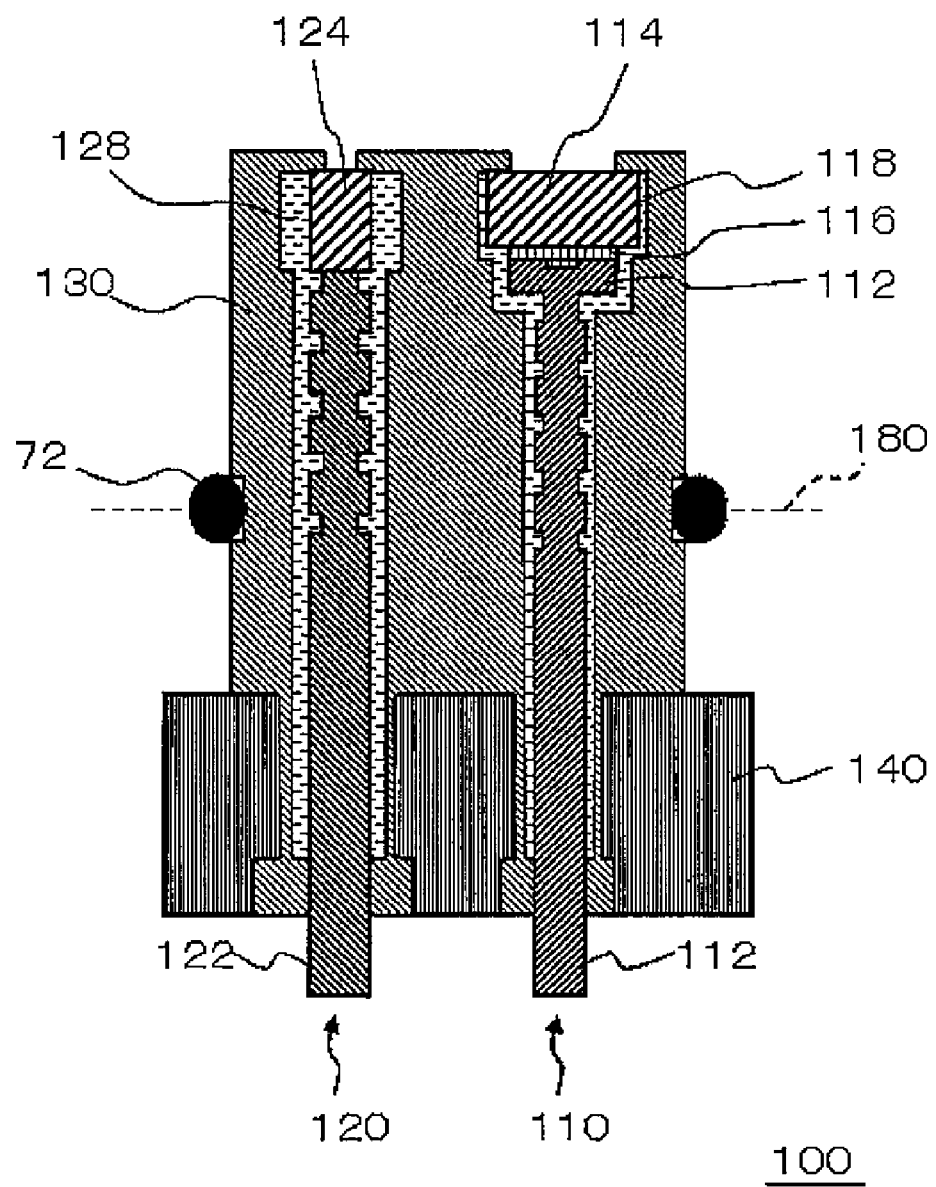
FIG. 3 is a cross-sectional view showing the detailed structure of the electrode assembly according to an embodiment of the present invention.

FIG. 3 is a cross-sectional view showing the detailed structure of the electrode assembly 100 according to an embodiment of the present invention.

The electrode assembly 100 includes a first electrode structure 110, a second electrode structure 120, non gas/fluid permeable insulating coatings 118 and 128, a cylindrical mold resin housing 130 and a cylindrical washer 140. The electrode structures 110 and 120 are molded into and extend axially through the cylindrical mold resin housing 130 in a sealed manner.

The electrode assembly 100 together with the O ring 72 forms high and low pressure condition boundary 180. Specifically, the O ring 72 forms a barrier to separate a high pressure region and a low pressure region when assembly 100 is deployed in a high pressure environment. That is, the part of the electrode assembly 100 closer to chamber 94 (above the level of the boundary 180 in FIG. 3) is in the high pressure condition and the part of the electrode assembly 100 below the level of the boundary 180 in FIG. 3 is in the low or normal condition.

The first electrode structure 110 includes an electrode 114 and a conductive pin 112 which is electrically and mechanically connected or bonded to the electrode 114 via a conductive connector 116 (shown in FIG. 2). Similarly to the first electrode structure 110, the second electrode structure 120 includes an electrode 124 and a conductive pin 122 which is connected to the electrode 124 to electrically connect the electrode 124 to the electrical lead 70 (shown in FIG. 2).

The electrode 114 or 124 may be a working electrode, a reference electrode or a counter/guard electrode. The electrode may be made of metal such as gold, silver, platinum, nickel or copper, or boron-doped diamond, or glassy or other modified carbon derivative. For example, the working electrode may be made of material such as platinum, gold, boron-doped diamond, or glassy or other modified carbon derivative. The reference electrode may be made of material such as silver coated with silver chloride/iodide or pseudo-platinum. The counter/guard electrode may be made of material such as platinum or boron doped diamond.

The conductive pins 112 and 122 may be made of material similar to the material from which the electrodes are made.

The conductive pins 112 or 122 may have uneven side surfaces. For example, the conductive pins 112 or 122 may have large portions each having a larger diameter and small portions each having a smaller diameter than that of the large portion, when viewed from the top surface, alternatively placed next to each other. With this structure, the side surfaces of the conductive pin 112 or 122 can have concave portions and protruding portions alternatively placed adjacent to each other. Therefore, when the cylindrical electrode assembly 100 is placed in a high temperature condition, and the materials constituting the cylindrical electrode assembly 100 are deformed by the thermal expansion, the delamination of the non gas/fluid permeable insulating coating 118 or 128, or the cylindrical mold resin housing 130 from the electrode structure 110 or 120 can be prevented.

Although the non gas/fluid permeable insulating coating 118 or 128 is described to fill the concave portion of the conductive pin 112 or 122, respectively, to make the side surfaces thereof smooth in FIG. 3, the coating 118 or 128 may be thin enough to reflect the uneven shape of the conductive pin 112 or 122 such that the outside side surfaces of the coating 118 or 128 may also have the uneven shape. In such a case, the delamination of the cylindrical mold resin housing 130 from the coating 118 or 128 can be prevented even when the cylindrical electrode assembly 100 is placed in a high temperature condition, and the materials constituting the cylindrical electrode assembly 100 are deformed by the thermal expansion.

The electrode structure may be formed by bonding the electrode to the conductive pin using the conductive connector 116 in a conventional method of assembling the conductive connector 116 of the electrode structure 110. The conductive connector 116 may be made of a material such as silver loaded conductive epoxy or high temperature solder but is not limited to such materials. The conductive connector 116 may be made of a pure solid metal when the electrode material is the metal described above.

Figure 4A:
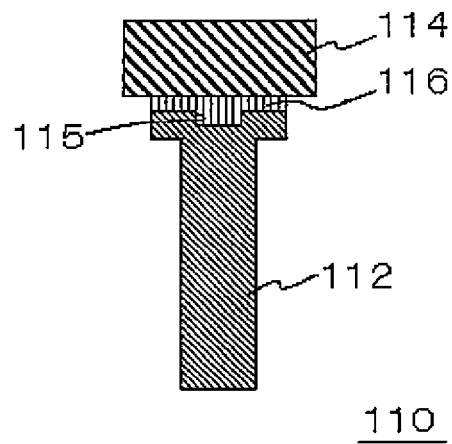
FIGS. 4A and 4B are cross-sectional views showing the connector structure according to embodiments of the present invention.

FIG. 4A is a cross-sectional view showing another example of the electrode structure 110. In this embodiment, there is provided a bonding groove 115 on a surface of the conductive pin 112 that faces the electrode 114. The bonding groove 115 is filled with the conductive connector 116 in order to ensure effective bonding of the electrode 114 and the conductive pin 112.

Figure 4B:
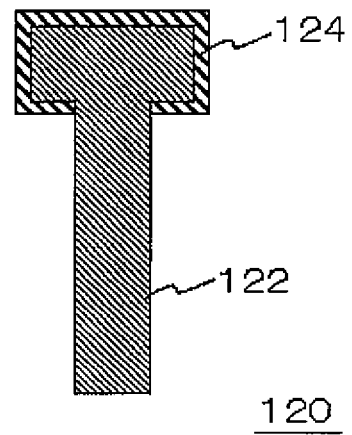

In other cases, the electrode structure may be formed by welding, brazing, electroplating and/or direct sputtering of one or more of the metals described above for the electrode material onto the appropriate surface of a conductive pin. FIG. 4B is a cross-sectional view showing an example of the connector structure 120. In this case, the electrode 124 is formed on the surface of the conductive pin 122 without an intervening connector.

The coating 118 or 128 may be an insulating layer which may be made of ceramic materials such as zirconia, amorphous silicon dioxide, or alumina, polymeric or glass fiber material or a combination of the foregoing materials.

Figure 5:
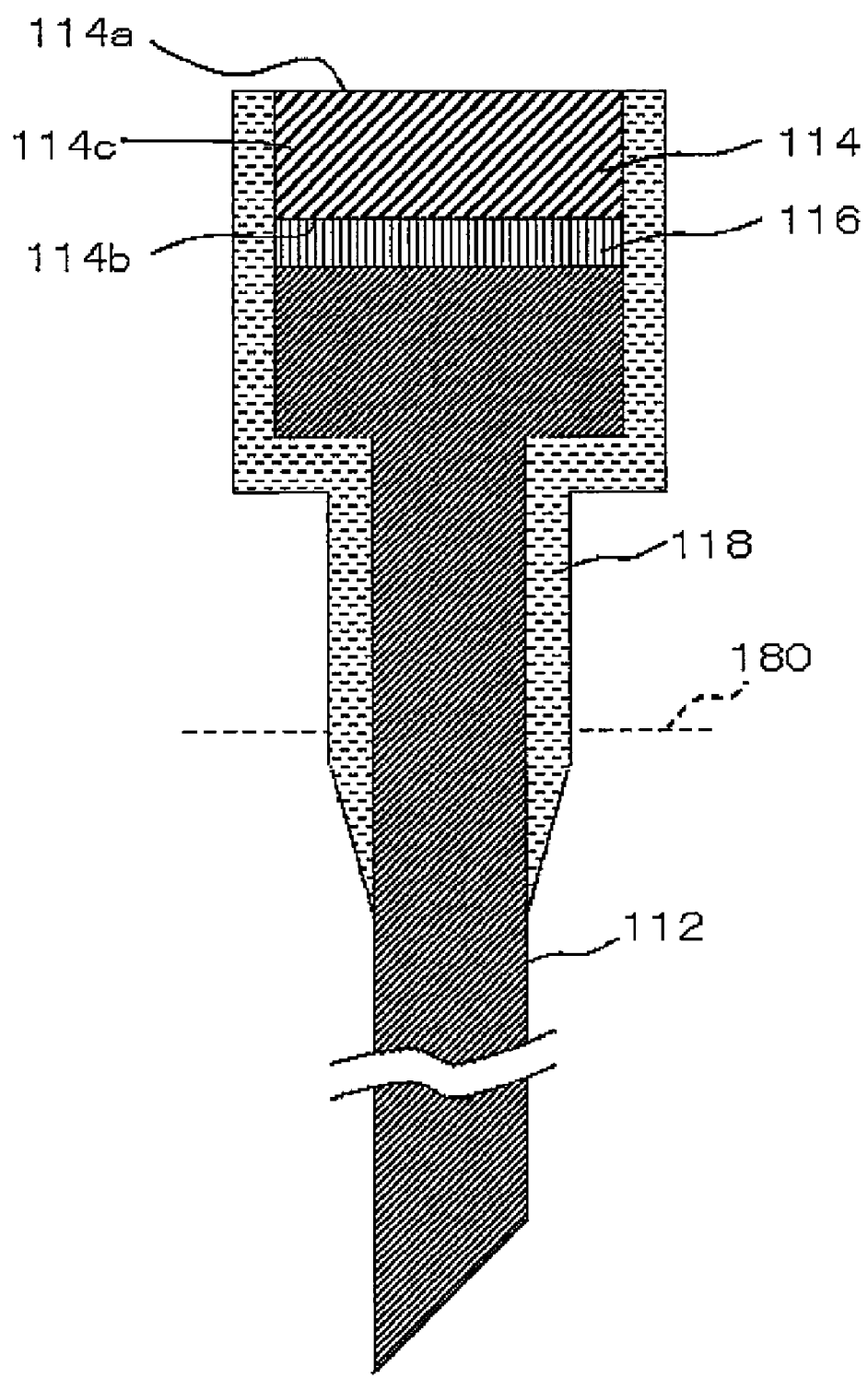
FIG. 5 is a cross-sectional view showing the structure of the electrode structure and the coating in detail according to an aspect of the present invention.

FIG. 5 is a cross-sectional view showing the structure of the electrode structure 110 and the coating 118 in detail.

The electrode 114 has a first surface (electrode surface) 114a which is to face a flow path of the hydrocarbon (the cylindrical space 94 shown in FIG. 2 in this embodiment, which contains the reaction fluid, as stated earlier), a second surface 114b opposite to the first surface 114a, and side surfaces 114c formed between the first surface 114a and the second surface 114b. The conductive pin 112 is connected to the second surface 114b of the electrode 114 via the conductive connector 116.

The coating 118 is formed to coat at least the side surfaces 114c of the electrode 114 and a part of the side surfaces of the conductive pin 112 closer to the electrode 114. For example, at least a part of the side surfaces of the conductive pin 112 placed closer to the high pressure region than the boundary 118 is coated with the coating 118. With this structure, the conductive pin 112 is protected from direct contact with the hydrocarbon even if the hydrocarbon penetrates into the mold resin housing 130.

Although it is not shown, the side surfaces of the rest of the conductive pin 112 closer to the lower pressure region may be plated for example by gold in order to be connected with the electrical leads 70 by soldering.

Referring back to FIG. 3, similarly to the first electrode structure 110, the second electrode structure 120 includes an electrode 124 having a first surface (electrode surface) which is to face a flow path of the hydrocarbon (the cylindrical space 94 shown in FIG. 2 in this embodiment), a second surface opposite to the first surface and side surfaces formed between the first surface and the second surface. The conductive pin 122 is connected to the second surface of the electrode 124.

Similarly, the coating 128 is formed to coat at least the side surfaces of the electrode 124 and a part of the side surface of the conductive pin 122 close to the electrode 124. The side surfaces of the rest of the conductive pin 122 closer to the lower pressure region may be plated for example by gold in order to be connected with the electrical leads 70 by soldering.

The washer 140 includes cylindrical holes in which the conductive pin 112 and the conductive pin 122 are respectively inserted to be held thereby.

The first electrode structure 110 and the second electrode structure 120 are molded in the mold resin housing 130. The mold resin housing 130 may be formed by a resin material such as polyetheretherketone, or polyetheretherketone—high glass transition temperature (PEEK-HT). In this embodiment, a thin layer of the mold resin material sleeves of the housing 130 are formed on a part of the top surfaces (first surfaces) of the electrodes 114 and 124, respectively, such that the edge of the top surfaces of the electrodes 114 and 124 are covered by the mold resin housing 130.

FIGS. 6 to 9 are cross-sectional views showing selected manufacturing steps in the fabrication of the electrode assembly 100.

First, the electrode structure 110 is formed by using the materials described above. Next, the surfaces of the electrode 114 except the top surface and a part of the surfaces of the conductive pin 112 closer to the electrode 114 are coated with the non gas/fluid permeable insulating coating 118. The electrode structure 120 is formed in accordance with a similar method as that of the electrode structure 110 and is coated by the non gas/fluid permeable insulating coating 128.

Figure 6:
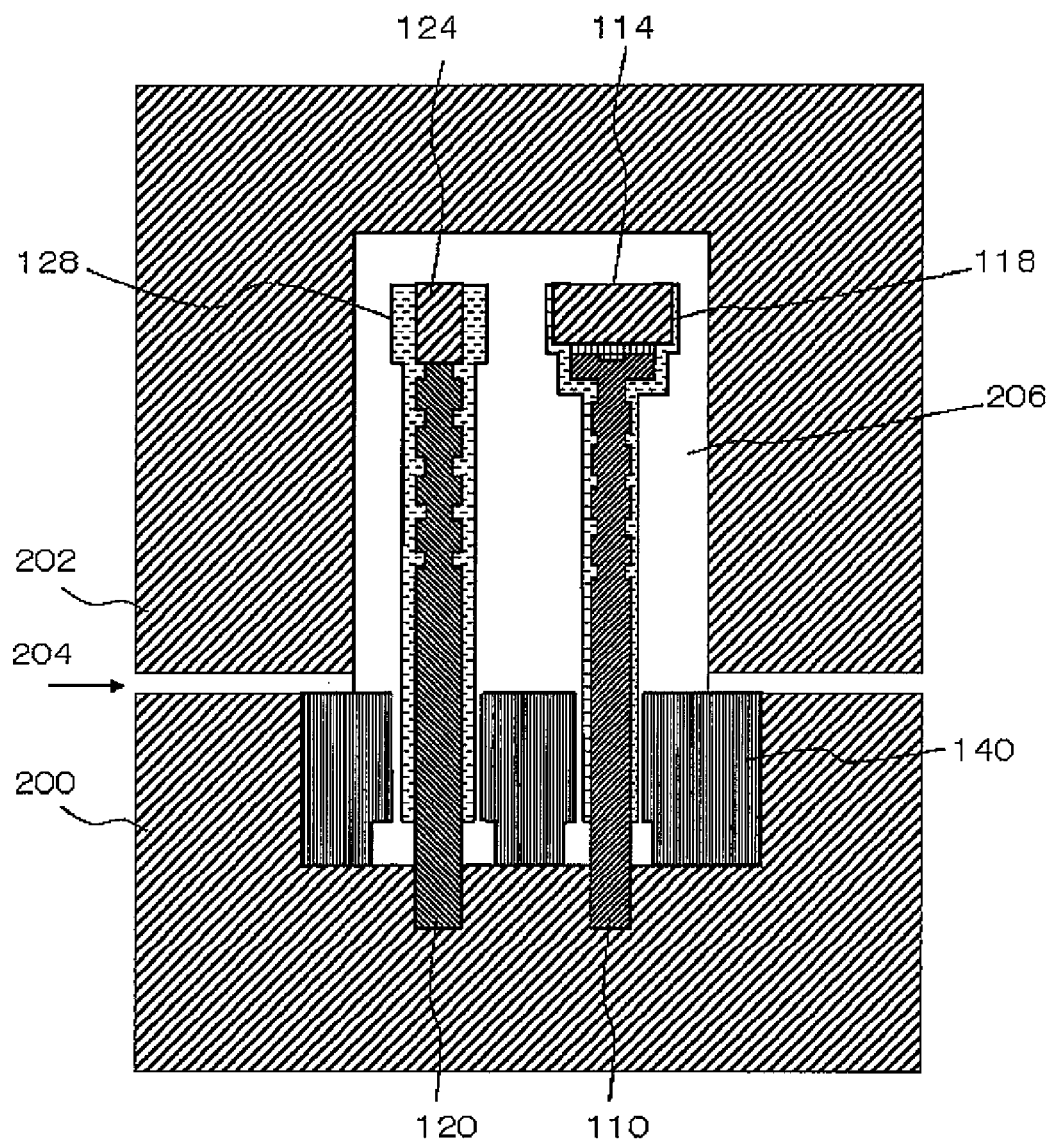
FIG. 6 is a cross-sectional view showing a manufacturing step in the fabrication of the electrode assembly according to an aspect of the present invention.

Then, the conductive washer 140 is placed in a bottom die 200, after which, the electrode structures 110 and 120 are respectively inserted into the holes of the conductive washer 140 such that the electrodes 114 and 124 are placed on top. Thereafter, an upper die 202 having a concave portion for forming mold resin housing 130 is placed on the bottom die 202 to form a space 206 therebetween, as shown in FIG. 6. Next, the resin material constituting the mold resin housing 130 is injected into the space 206 to mold the electrode structures 110 and 120.

Figure 7:
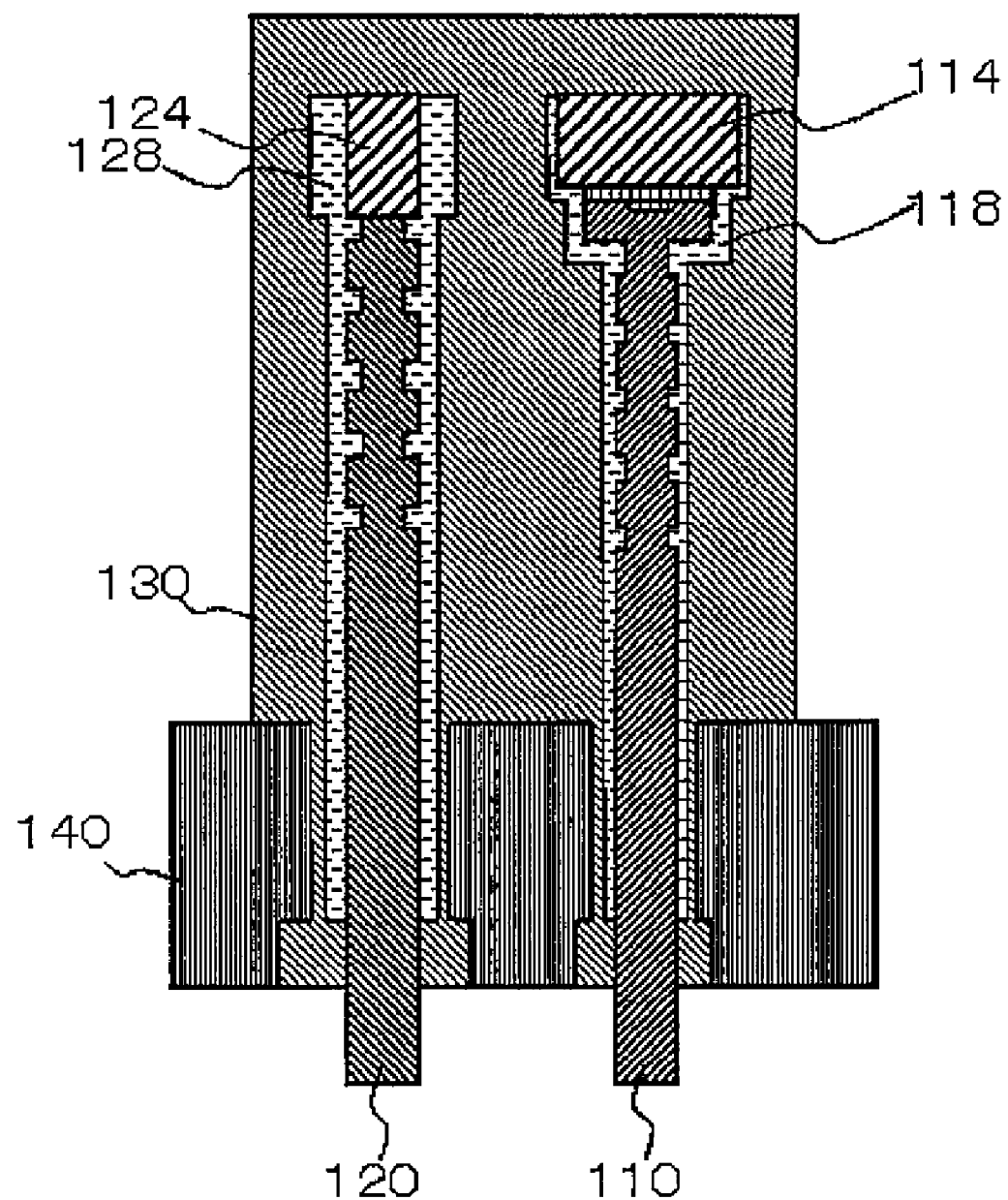
FIG. 7 is a cross-sectional view showing one intermediate manufacturing step in the fabrication of the electrode assembly according to an aspect of the present invention.

FIG. 7 shows the molded structure. At his time, the mold resin material of the housing 130 is formed over the entire top surfaces of the electrodes 114 and 124 thicker than that of the mold resin material sleeves left on the part of the top surfaces of the electrodes 114 and 124, as shown in FIG. 3.

Figure 8:
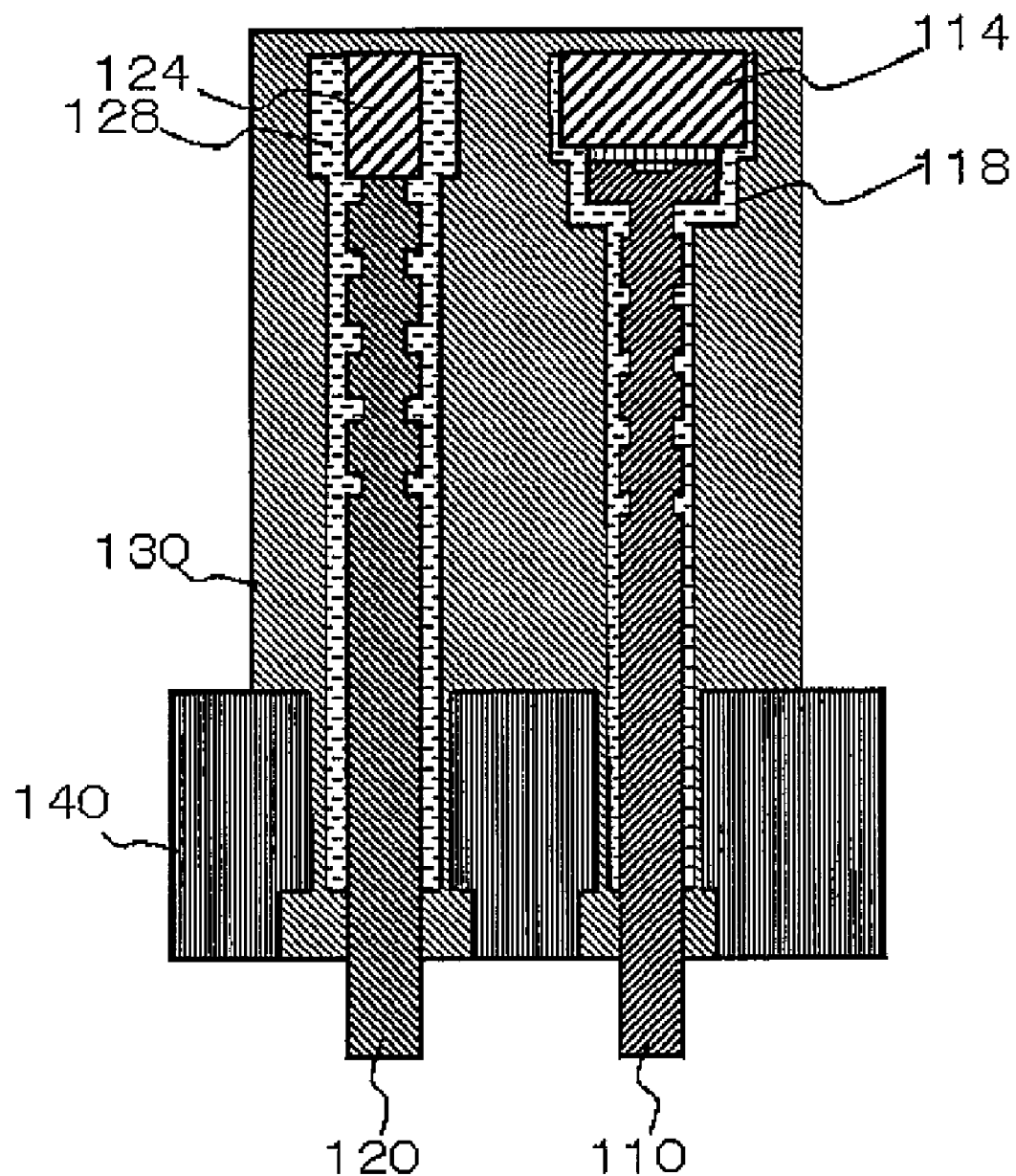
FIG. 8 is a cross-sectional view showing another intermediate manufacturing step in the fabrication of the electrode assembly according to an aspect of the present invention.

Following this step, the thickness of the mold resin material on the electrode surface is reduced through successive polishing steps down to the same thickness as that of the mold resin material sleeves extending over the top surfaces of the electrodes 114 and 124, as shown in FIG. 3. This structure is shown in FIG. 8.

Figure 9:
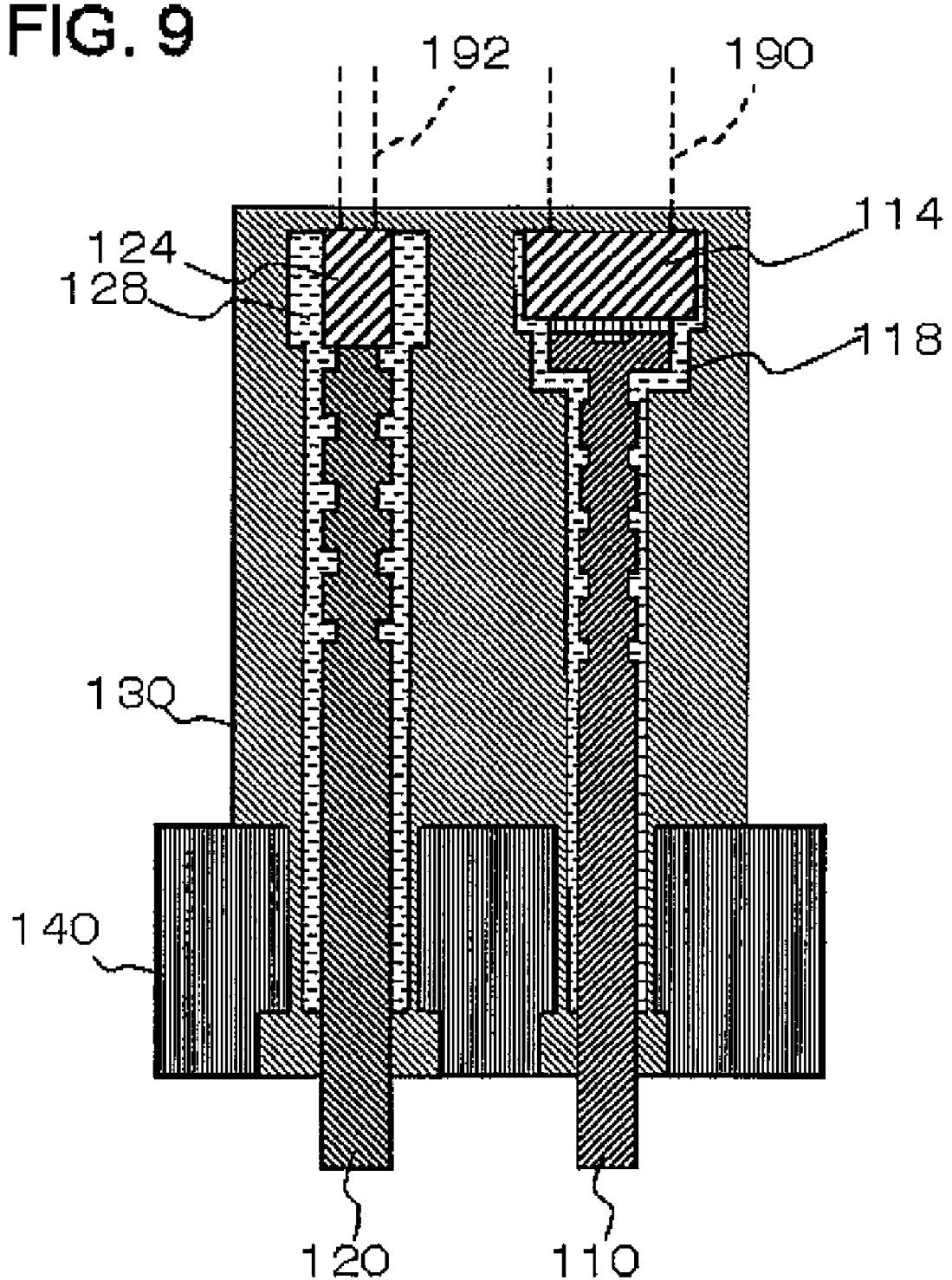
FIG. 9 is a cross-sectional view showing yet another manufacturing step in the fabrication of the electrode assembly in relation to the diameters of the bores according to an aspect of the present invention.

Next, cylindrical bores 192 and 190 are drilled into the upper portion of the mold resin material to expose parts of the top surfaces of the electrodes 114 and 124 by a combination of drilling and polishing steps on the respective electrode surfaces as shown in FIG. 9. As a result, the thin layer of the mold resin material sleeves are left on the top surfaces of the electrodes 114 and 124 as shown in FIG. 3. This arrangement can prevent the penetration of the electrolyte or buffer fluids into the sides of the conductive pins 112 and 122. As a result of the interface between the electrode 114 or 124 and the coating 118 or 128 being covered by the mold resin material of the housing 130, the penetration of the electrolyte or buffer fluids and the penetration of the hydrocarbon into the sides of the conductive pins 112 and 122 can be effectively prevented.

In addition, as the dimension of the exposed portion of the electrode 114 or 124 is not determined by the original diameter of the electrode 114 or 124 but rather by the diameter of the bore 190 or 192, respectively, it is possible to set the dimension of the exposed portion within a target range. Thus, accurate measurement can be conducted.

Next, a series of polishing procedures are performed, using compounds of decreasing particle size, such as alumina and/or carbon-based polishing pastes, in order to remove any contaminant on the surface of the electrodes 114 and 124. The lower part of the conductive pins 112 and 122 serves as an external electrical connection.

Although only two electrode structures are shown in FIGS. 3 and 6-9, the electrode assembly 100 may include more electrode structures, each one including at least the electrode and the conductive pin.

Figure 10:
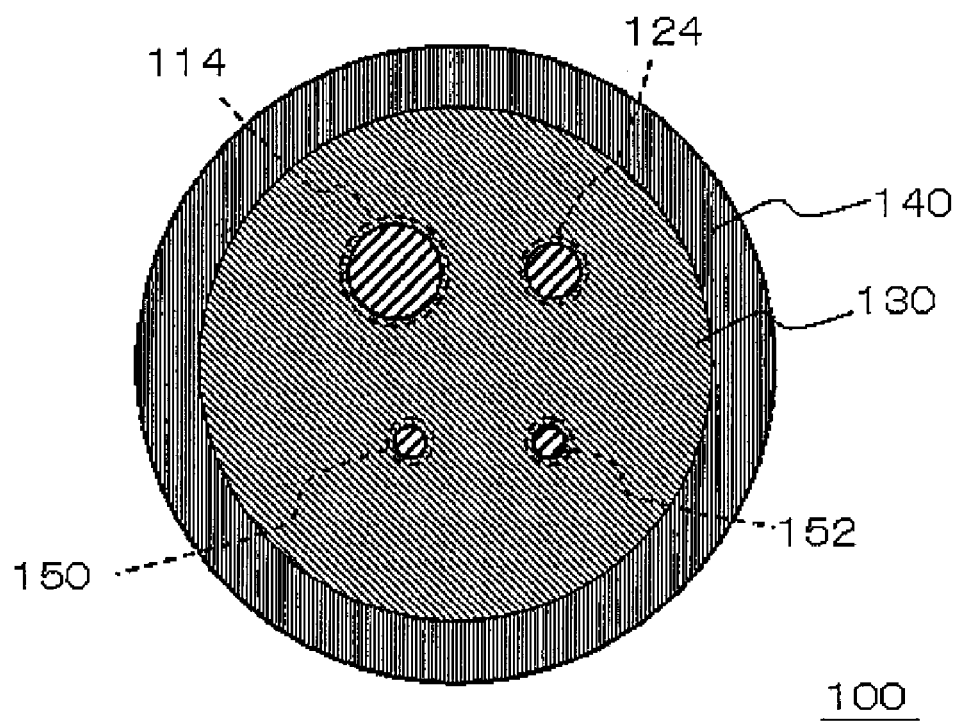
FIG. 10 is a top view of an electrode assembly according to an embodiment of the present invention.
Figure 11:
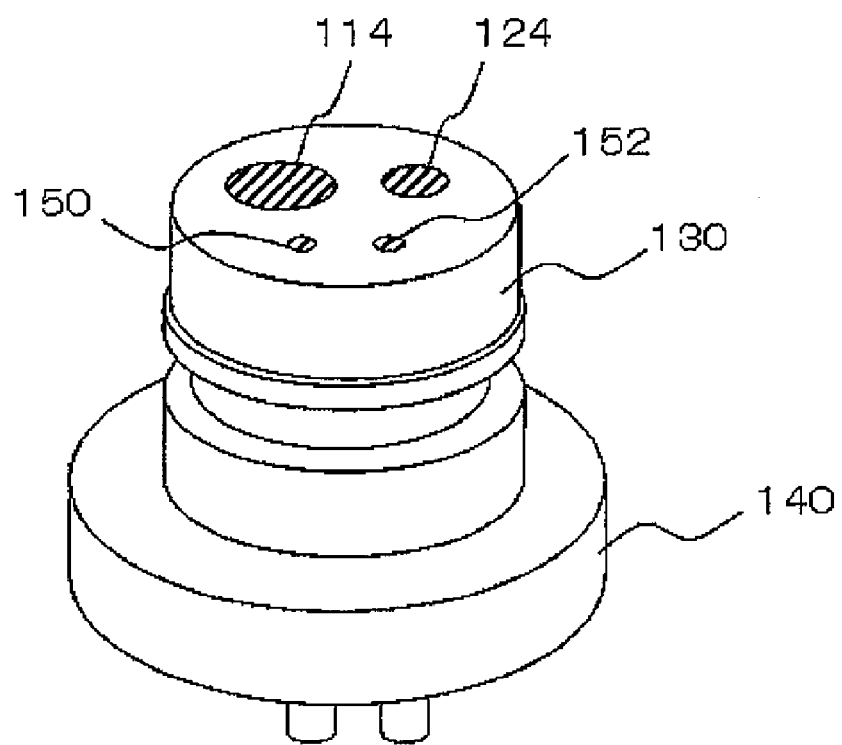
FIG. 11 is a perspective external view of an electrode assembly according to an embodiment of the present invention.

FIG. 10 is a top view showing the structure of the electrode assembly 100. As shown, the electrode assembly 100 further includes electrodes 150 and 152 in addition to the electrodes 114 and 124. FIG. 11 is a schematic view showing the structure of the electrode assembly 100 shown in FIG. 10.

Referring to FIG. 10, the electrodes 114, 124, 150, and 152 are shown by dotted line. Each of the electrodes 114, 124, 150, and 152 has a larger diameter than that of the hole formed in the cylindrical mold resin housing 130.

The electrode 152 may be the working electrode and the electrode 150 may be the counter electrode of the working electrode. The electrode 124 may be the reference electrode and the electrode 114 may be the counter electrode of the reference electrode.

Referring back to FIG. 2, in operation, the sensor 30 fits in a cylindrical recess in a block (not shown) through which the conduit 26 passes, with the flow path 56 in alignment with the conduit 26, and with sealing provided by the O-ring seal 92 in the groove 96 in the upper portion 44 of the housing 40 of the sensor 30. The upper side of the membrane 82 in the sensor 30 is thus exposed via the flow path 56, the ports of the housing member 78, the flow path of the housing member 80 and the duct 88 to the hydrocarbons in the conduit 26. Suitable electronic measurement equipment is used to apply a cyclically varying potential between the working electrode and the reference electrode to measure the peak currents flowing between the working electrode and the counter electrode.

In this embodiment, before being molded into the mold resin housing, the electrode structure is coated with the non gas/fluid permeable insulating coating. Therefore, the conductive pin can be protected from direct contact with the hydrocarbon even if the hydrocarbon penetrates into the mold resin housing when the electrode faces high pressure and high temperature conditions. In addition, as the electrode structure is molded in the mold resin housing, complete isolation from the hydrocarbon can be further ensured.

Alternatively, instead of using the mold resin housing, a metal body can be used to attain enhanced robustness and mechanical rigidity. In such a case, the electrode structures are coated with the non gas/fluid permeable insulating coating prior to hermetic attachment to the metal body. Hermetic attachment techniques have been widely adapted in various commercial electrical connectors as disclosed in international patent publication numbers WO2005083846 and WO2005020272 and U.S. Pat. No. 6,582,251A.

The electrochemical sensor 30 may include a pressure balancing function that controls the pressures on both sides of the membrane 82, balancing them such that the pressure of the liquid reagents in the chamber 94 is substantially equal to the pressure of the hydrocarbons in the flowpath 56, thus substantially eliminating the pressure differential across the membrane 82, as described in GB 2,371,651A.

Figure 12:
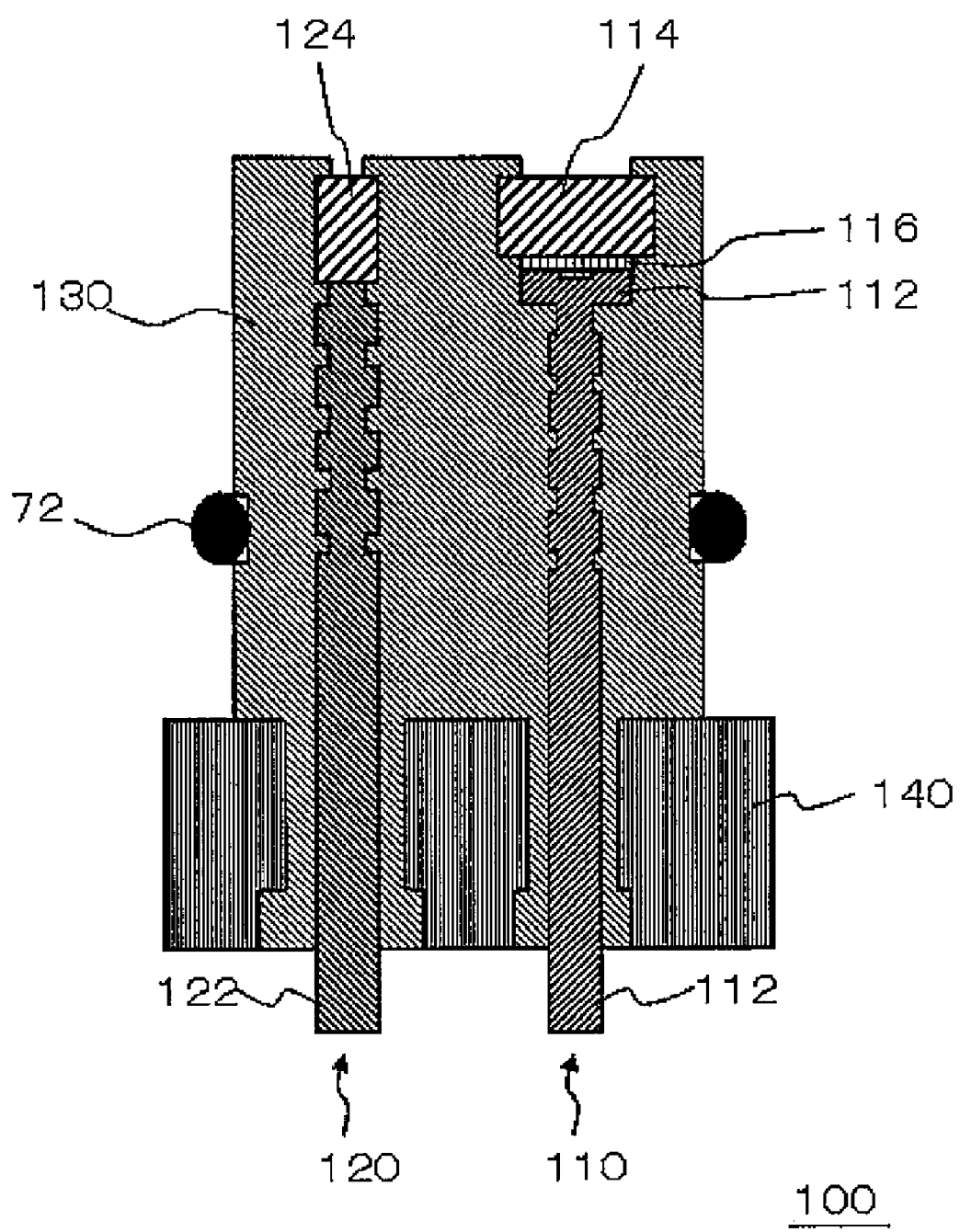
FIG. 12 is a cross-sectional view of an electrode assembly according to an embodiment of the present invention.

FIG. 12 is a cross-sectional view showing the detailed structure of the electrode assembly 100 according to another embodiment of the present invention. The electrode assembly 100 of this embodiment is different from that of the previous embodiments herein in that the non gas/fluid permeable insulating coatings are not formed at the side surfaces of the electrode structures.

Isolation from the hydrocarbon can be obtained, even with the structure of this embodiment, since the electrode structures are molded in the mold resin housing.

It bears emphasizing that the designs and concepts disclosed herein are applicable to environments other than a wellbore, for example, for environmental conditions that require operation between a high and low pressure condition boundary. In this, it is contemplated as a feature of the present invention that wireline logging, production logging, permanent monitoring, logging-while-drilling (LWD), and uphole applications, such as in a separator which is located uphole to separate fluids (e.g., liquid and gas) by density difference, have applicability to the present invention. The electrochemical sensor disclosed herein may be utilized in a variety of setting having high pressure and/or high temperature conditions such as those described herein.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. An electrochemical sensor comprising:
a bulkhead electrode assembly including a cylindrical housing and a cylindrical electrode structure placed in said cylindrical housing; and
a seal ring extending around said cylindrical housing and said cylindrical electrode structure to separate a high pressure region and a low pressure region of said cylindrical electrode structure;
said cylindrical electrode structure including a cylindrical conductive pin extending from the high pressure region to the low pressure region, and an electrode connected to one end of said cylindrical conductive pin at the high pressure region and having an electrode surface positioned for exposure to a flow path of a fluid or a gas in said high pressure region, whereby an electrochemical reaction occurs at said electrode surface exposed to said fluid or said gas; and
an insulating coating over at least a part of a radial surface of said cylindrical conductive pin positioned adjacent to the end connected to said electrode, said insulating coating being impermeable to said fluid or said gas and configured to protect said cylindrical conductive pin from direct contact with said fluid or said gas.

2. The electrochemical sensor as set forth in claim 1, wherein at least an axial surface of said electrode is coated with said insulating coating.

3. The electrochemical sensor as set forth in claim 1, wherein said insulating coating is formed of one or more materials selected from a group including a ceramic material a polymeric material and a glass fiber material.

4. The electrochemical sensor as set forth in claim 1, wherein said cylindrical housing is formed of a mold resin housing in which said electrode structure is molded.

5. The electrochemical sensor as set forth in claim 4, wherein said mold resin housing is configured to cover all edges of said electrode directly adjacent said electrode surface.

6. The electrochemical sensor as set forth in claim 1, wherein the axial surface of said cylindrical conductive pin includes an alternating pattern along a lengthwise direction of the axial surface, the alternating pattern including a receded portion extending about a circumference of the cylindrical conductive pin adjacent a protruding portion extending about the circumference of the cylindrical conductive pin.

7. The electrochemical sensor as set forth in claim 6, wherein the receded portion is one of concave, beveled or includes angles of 90 degrees, and the protruding portion is one of convex, beveled or includes angles of 90 degrees.

* * * * *